(12) United States Patent
Kim et al.

(10) Patent No.: US 9,582,683 B2
(45) Date of Patent: *Feb. 28, 2017

(54) APPARATUS AND METHOD FOR MANAGING HEALTH DATA

(71) Applicant: Samsung Electronics Co. Ltd., Suwon-si, Gyeonggi-do (KR)

(72) Inventors: Do-Young Kim, Hwaseong-si (KR); In-Kyo Kim, Seoul (KR); Jeong-Je Park, Hwaseong-si (KR); Kwang-Hyeon Lee, Seoul (KR); Nae-Hyun Lim, Seoul (KR); Hyoung-Kyu Lim, Seoul (KR); Yong Chang, Seongnam-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 15/041,645

(22) Filed: Feb. 11, 2016

(65) Prior Publication Data
US 2016/0162705 A1   Jun. 9, 2016

Related U.S. Application Data

(63) Continuation of application No. 14/017,003, filed on Sep. 3, 2013, now Pat. No. 9,294,472.

(30) Foreign Application Priority Data

Aug. 31, 2012   (KR) .................. 10-2012-0096550

(51) Int. Cl.
*H04L 29/06* (2006.01)
*G06F 21/62* (2013.01)
(Continued)

(52) U.S. Cl.
CPC ......... *G06F 21/6245* (2013.01); *G06F 19/322* (2013.01); *G06F 21/44* (2013.01);
(Continued)

(58) Field of Classification Search
CPC .... G06F 19/322; G06F 21/44; G06F 21/6245; G06F 19/327; G06F 21/577; H04L 63/0428; H04L 63/083; H04L 67/12
(Continued)

(56) References Cited

U.S. PATENT DOCUMENTS

2002/0049684 A1* 4/2002 Nagamoto .......... A61B 5/0002
706/1
2003/0039362 A1   2/2003 Califano et al.
(Continued)

FOREIGN PATENT DOCUMENTS

JP    2008-197742 A    8/2008
KR    10-2009-0127480 A    12/2009
(Continued)

*Primary Examiner* — Yogesh Paliwal
(74) *Attorney, Agent, or Firm* — Jefferson IP Law, LLP

(57) ABSTRACT

An apparatus and method for managing health data through a user terminal are provided. The method includes inputting a user terminal number for identifying the user terminal, and information of a medical instrument for measuring the health data to a management server interworked with the user terminal, receiving, by a receiver, a security type table mapped onto the user terminal number and comprising a security type code for instructing the health data which the medical instrument has measured to be stored in a first memory without security or in a second memory with security, from the management server, and storing the health data in the first memory or the second memory, which the security type code instructs, through determining the security type code of the security type table when the health data is received from the medical instrument.

25 Claims, 9 Drawing Sheets

(51) Int. Cl.
  *H04L 29/08* (2006.01)
  *G06F 19/00* (2011.01)
  *G06F 21/44* (2013.01)

(52) U.S. Cl.
  CPC ........ *H04L 63/0428* (2013.01); *H04L 63/083* (2013.01); *H04L 67/12* (2013.01)

(58) Field of Classification Search
  USPC ........................................................... 726/5
  See application file for complete search history.

(56) References Cited

U.S. PATENT DOCUMENTS

| | | |
|---|---|---|
| 2004/0186746 A1* | 9/2004 | Angst .................... G06F 19/322 705/3 |
| 2005/0114689 A1 | 5/2005 | Strom et al. |
| 2006/0155583 A1 | 7/2006 | Teshima et al. |
| 2006/0155990 A1 | 7/2006 | Katsube et al. |
| 2008/0319799 A1 | 12/2008 | Knowlton |
| 2009/0030286 A1 | 1/2009 | Amital |
| 2009/0055924 A1 | 2/2009 | Trotter |
| 2009/0097623 A1* | 4/2009 | Bharadwaj ........... H04M 11/027 379/106.02 |
| 2010/0292556 A1 | 11/2010 | Golden |

FOREIGN PATENT DOCUMENTS

| | | |
|---|---|---|
| KR | 10-2010-0041660 A | 4/2010 |
| KR | 10-2011-0075848 A | 7/2011 |

* cited by examiner

APPARATUS AND METHOD FOR MANAGING HEALTH DATA

CROSS-REFERENCE TO RELATED APPLICATION(S)

This application is a continuation application of prior application Ser. No. 14/017,003, filed on Sep. 3, 2013, which claimed the benefit under 35 U.S.C. §119(a) of a Korean patent application filed on Aug. 31, 2012 in the Korean Intellectual Property Office and assigned Serial No. 10-2012-0096550, the entire disclosure of which is hereby incorporated by reference.

TECHNICAL FIELD

The present disclosure relates to health data. More particularly, the present disclosure relates to an apparatus and a method for managing health data.

BACKGROUND

As interest in healthcare continues to increase, necessities for management of health data are also gradually increasing. Further, in recent years, demands for services by which smart phone users can manage their own health data through a smart phone are increasing together with a rapid increase in the number of smart phone users.

Services by which health data measured through a medical instrument, such as a body weight scale, a blood pressure meter, a blood sugar meter, a electrocardiograph, or a blood analyzer is transferred to an Information Technology (IT) device, such as a smart phone by applying a Near Field Communication (NFC) technology, and users manage their own health data are currently used. In addition, demands for the services are expected to continuously increase together with an increase in the number of smart phones in use.

Meanwhile, according to types of health data, some can be made available to anyone, whereas others should be made available to a specific group, such as a medical team. However, since the health data is currently available to be shared with anyone, the private health data is not shared with only the medical team but with other persons, which causes problems, such as private information exposure on the Internet, or improper use of the private health data by companies hiring employees. Moreover, when a smart phone storing the health data is lost, problems in management of private health data can occur.

Therefore, a need exists for a method capable of addressing the problems in management of the health data.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide an apparatus and a method for managing health data by classifying the health data according to security types.

In accordance with an aspect of the present disclosure, a method of managing health data through a user terminal is provided. The method includes inputting a user terminal number for identifying the user terminal, and information of a medical instrument for measuring the health data to a management server interworked with the user terminal, receiving, by a receiver, a security type table mapped onto the user terminal number and comprising a security type code for instructing the health data which the medical instrument has measured to be stored in a first memory without security or in a second memory with security, from the management server, and storing the health data in the first memory or the second memory, which the security type code instructs, through determining the security type code of the security type table when the health data is received from the medical instrument.

In accordance with another aspect of the present disclosure, a method of managing health data through a management server interworked with a user terminal is provided. The method includes receiving, by a receiver, a user terminal number for identifying the user terminal and information of a medical instrument for measuring the health data, from the user terminal, determining, by a controller, whether or not a security type code instructs the health data, which the medical instrument measures to be stored in a first memory without security or a second memory with security is registered in the management server, and issuing, by a management unit, a security type table mapped onto the user terminal number based on the security type code to transmit the issued security type table to the user terminal, when the security type code is registered in the management server.

In accordance with another aspect of the present disclosure, a method of managing health data measured by a medical instrument through a hospital server is provided. The method includes detecting, by a controller, a user terminal number for identifying a user terminal and a table code of a security type table, which the user terminal manages, from the user terminal, determining, by the controller, whether or not the detected table code coincides with a table code of a security type table mapped onto the user terminal number, and sharing, by a transmitter, health data stored in a memory with security among health data which the user terminal manages with the user terminal, when the detected table code coincides with the table code of the security type table mapped onto the user terminal number.

In accordance with another aspect of the present disclosure, a user terminal for managing health data is provided. The user terminal includes a first memory without security, a second memory with security, a transmitter configured to transmit a user terminal number for identifying the user terminal and information of a medical instrument for measuring the health data to a management server interworked with the user terminal, a receiver configured to receive a security type table mapped onto the user terminal number and comprising a security type code for instructing the health data which the medical instrument has measured to be stored in the first memory or the second memory, from the management server, and to receive the health data from the medical instrument, and a controller configured to determine the security type code of the security type table, and to instruct the health data to be stored in the first memory or the second memory which the security type code indicates, when the health data is received.

In accordance with another aspect of the present disclosure, a management server for managing health data is provided. The management server includes a receiver configured to receive a user terminal number for identifying a user terminal and information of a medical instrument for measuring the health data, from the user terminal, a controller configured to determine whether or not a security type code instructs the health data which the medical instrument measures to be stored in a first memory without security or a second memory with security is registered in the management server, a management unit configured to issue a security type table mapped onto the user terminal number based on the security type code, when the security type code is registered in the management server, and a transmitter configured to transmit the security type table to the user terminal.

In accordance with another aspect of the present disclosure, a hospital server for managing health data measured by a medical instrument is provided. The hospital server includes a controller configured to detect a user terminal number for identifying a user terminal and a table code of a security type table which the user terminal manages, from the user terminal, and to determine whether or not the detected table code coincides with a table code of a security type table mapped onto the user terminal number, and a transmitter configured to share health data stored in a memory with security among health data which the user terminal manages with the user terminal, when the detected table code coincides with the table code of the security type table mapped onto the user terminal number.

The present disclosure proposes a method of managing health data by classifying the health data according to security types, thereby overcoming the problem caused by sharing security required health data with others.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

In an embodiment of the present disclosure which will be described below, a method in which, when a user terminal purchases a medical instrument and stores health data measured through the medical instrument, the corresponding data is stored and managed in mutually different memories according to security types of health data will be proposed. For example, a method of storing and managing the corresponding data in mutually different memories according to whether or not the health data is general data, which can be available to anyone, or security data, which should be available to a specific group, such as a medical team, will be proposed.

Further, in an embodiment of the present disclosure which will be described below, a security type table will be proposed for storing and managing health data in mutually different memories according to security types. The security type table may be issued such that the corresponding security types may be classified by medical instruments or measured health data.

Figure 1:
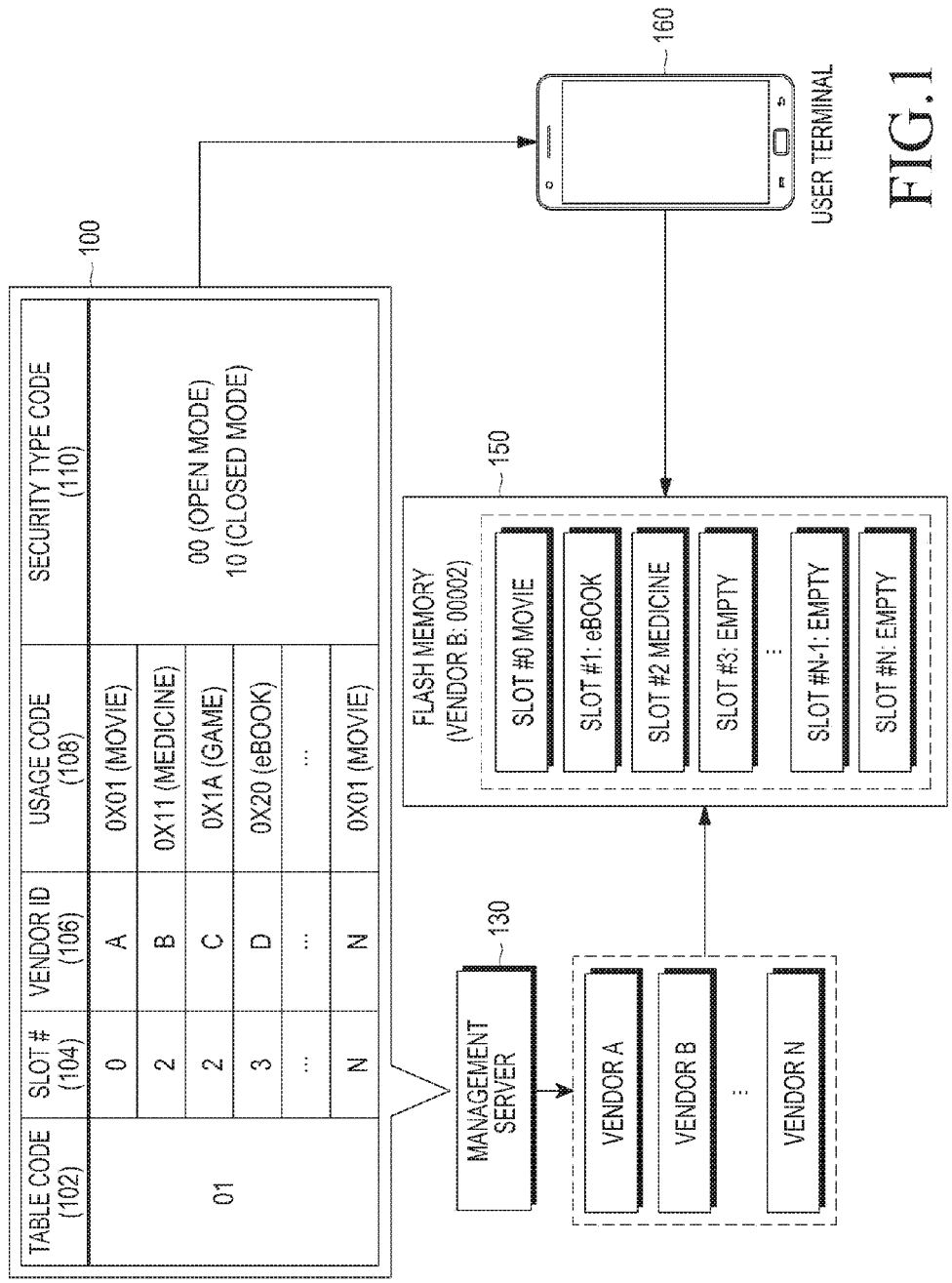
FIG. 1 illustrates a security type table for classifying security types according to medical instruments according to an embodiment of the present disclosure.

FIG. 1 illustrates a security type table for classifying security types according to medical instruments according to an embodiment of the present disclosure.

Referring to FIG. 1, a user terminal 160 purchases a medical instrument for measuring a user's health status, for example, a body weight scale, a blood pressure meter, a blood sugar meter, a electrocardiograph, a blood analyzer, or the like, through a management server 130, and the management server 130 issues and manages a security type table 100 corresponding to the medical instrument. Here, although descriptions will be given with an assumption that the user terminal 160 is a smart phone, it is apparent that the user terminal 160 may be any other IT device. Further, it is assumed that the medical instrument is purchased through a sensor shop of an application executed in the smart phone. Here, the sensor shop is a store where the medical instrument is sold, and is managed through the management server 130.

The security type table 100 is a table for indicating security types of health data, for example, a weight, a blood pressure, a blood sugar, an electrocardiogram, a blood analysis result, or the like, which are measured by the medical instruments, and includes information, such as a table code 102, slot numbers (slot #) 104, vendor Identifiers (IDs) 106, usage codes 108, and security type codes 110.

The table code 102 denotes a code for identification of the security type table 100, the slot numbers (slot #) 104 denote slot numbers of slots constituting a flash memory 150, and the vendor IDs 106 denote IDs for identifying vendors of the flash memory 150.

Here, usage of the slots constituting the flash memory 150 may be differentially set according to vendors, and the usage codes 108 denote usage of the respective slots. For example, '0x01' denotes that slot #0 constituting a flash memory of vendor A and slot #N constituting a flash memory of vendor N are used for storing movie related data, '0x 11' denotes that slot #2 constituting a flash memory of vendor B is used for storing medicine related data, that is, health data, '0x1A' denotes that slot #2 constituting a flash memory of vendor C is used for storing game related data, and '0x20' denotes that slot #3 constituting a flash memory of vendor D is used for storing electronic-book (e-book) related data.

The security type codes 110 denote security types of health data measured through the medical instrument. For example, '00' denotes that a type of measured health data corresponds to a type of general data so that the measured health data should be stored through an open mode, and '10' denotes that a type of measured health data corresponds to a type of security data so that the measured health data should be stored through a closed mode. The open mode is a mode of instructing the corresponding health data to be stored in an open memory, for example, a Universal Subscriber Identifier Module (USIM) chip, which can be shared with anyone, and the closed mode is a mode of instructing the corresponding health data to be stored in a memory with security, for example, an Enhanced Media Identification (EMID) flash memory, which can be shared with a specific group. For example, in the closed mode, the health data is stored in the memory with security so that information stored in the memory cannot be shared before an inherent ID is input, making it possible to basically prevent external access to the health data.

For example, it is assumed that the security type table 100 is created to correspond to a blood analyzer, and at this time, the security type code 110 of the health data which the usage code 108 '0x11' denotes is set to code '10' denoting the closed mode. Accordingly, the user terminal 160 receiving the security type table 100 from the management server 130 stores a blood analysis result measured through the blood analyzer in the memory with security.

Meanwhile, the management server 130 manages a plurality of flash memories inherently constituted according to vendors, and as an example of the flash memory 150, a configuration of a flash memory of vendor B is illustrated. The flash memory 150 is formed of N slots, for example, slot #0 in which movie related data is stored, slot #1 in which e-book related data is stored, slot #2 in which medicine related data is stored, and the like, and it is apparent that data stored in the slots may be differently set according to the vendors.

Figure 2:
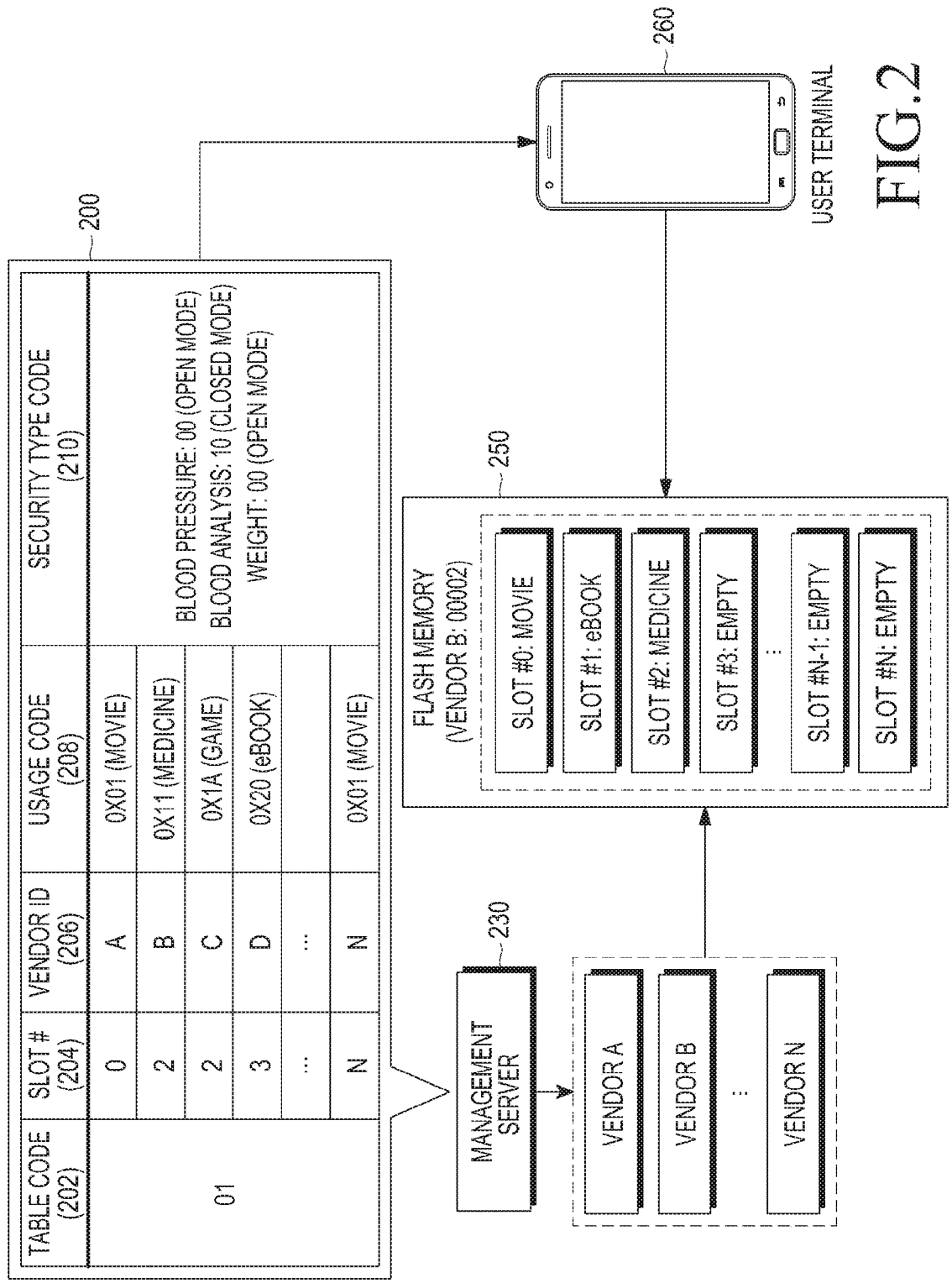
FIG. 2 illustrates a security type table for classifying security types according to measurable health data in a medical instrument according to an embodiment of the present disclosure.

FIG. 2 illustrates a security type table for classifying security types according to measurable health data in a medical instrument according to an embodiment of the present disclosure.

Referring to FIG. 2, a user terminal 260 purchases a medical instrument for measuring a user's health status through a management server 230, and the management server 230 issues and manages a security type table 200 corresponding to the medical instrument. In FIG. 2, it is assumed that one medical instrument may measure a plurality of health data unlike in FIG. 1, and thus, the security type table 200 is made such that security types may be classified according to measurable health data in the medical instrument.

Here, although descriptions will be given with an assumption that the user terminal 260 is a smart phone, it is apparent that the user terminal 260 may be any other IT device. Further, it is assumed that the medical instrument is purchased through a sensor shop of an application executed in the smart phone.

The security type table 200 is a table for indicating the security types of the health data which are measured in the medical instrument, and includes information, such as a table code 202, slot numbers (slot #) 204, vendor IDs 206, usage codes 208, and security type codes 210.

The table code 202 denotes a code for identification of the security type table 200, the slot numbers (slot #) 204 denote slot numbers of slots constituting a flash memory 250, and the vendor IDs 206 denote IDs for identifying vendors of the flash memory 250.

Here, usage of the slots constituting the flash memory 250 may be differentially set according to vendors, and the usage codes 208 denote usage of the respective slots. For example, '0x01' denotes that slot #0 constituting a flash memory of vendor A and slot #N constituting a flash memory of vendor N are used for storing movie related data, '0x11' denotes that slot #2 constituting a flash memory of vendor B is used for storing medicine related data, that is, health data, '0x1A' denotes that slot #2 constituting a flash memory of vendor C is used for storing game related data, and '0x20' denotes that slot #3 constituting a flash memory of vendor D is used for storing e-book related data.

The security type codes 210 denote security types of a plurality of health data measured through the medical instrument. For example, '00' denotes that a type of measured health data corresponds to a type of general data so that the measured health data should be stored through an open mode, and '10' denotes that a type of measured health data corresponds to a type of security data so that the measured health data should be stored through a closed mode. Here, assuming that the medical instrument corresponding to the security type table 200 measures a blood pressure, a blood analysis result, and a weight, the security type code 210 of the blood pressure and the weight which the medical instrument has measured is set to code '00' denoting that the measured blood pressure and weight should be stored through an open mode, and the security type code 210 of the blood analysis result which the medical instrument has measured is set to code '10' denoting that the measured blood analysis result should be stored through a closed mode. Accordingly, the user terminal 260 receiving the security type table 200 from the management server 230 stores the health data measured through the medical instrument in an open memory or in a memory with security according to the sorts of the health data. For example, the user terminal stores the blood pressure and the weight in a USIM chip corresponding to the open memory which can be shared with anyone, and stores the blood analysis result in an EMID flash memory corresponding to the memory with security which can be shared with a specific group, among the health data measured through the medical instrument.

Meanwhile, the management server 230 manages a plurality of flash memories inherently constituted according to vendors, and as an example of the flash memory 250, a configuration of a flash memory of vendor B is illustrated. The flash memory 250 is formed of N slots, for example, slot #0 in which movie related data is stored, slot #1 in which e-book related data is stored, slot #2 in which medicine related data is stored, and the like, and it is apparent that data stored in the slots may be differently set according to the vendors.

Figure 3:
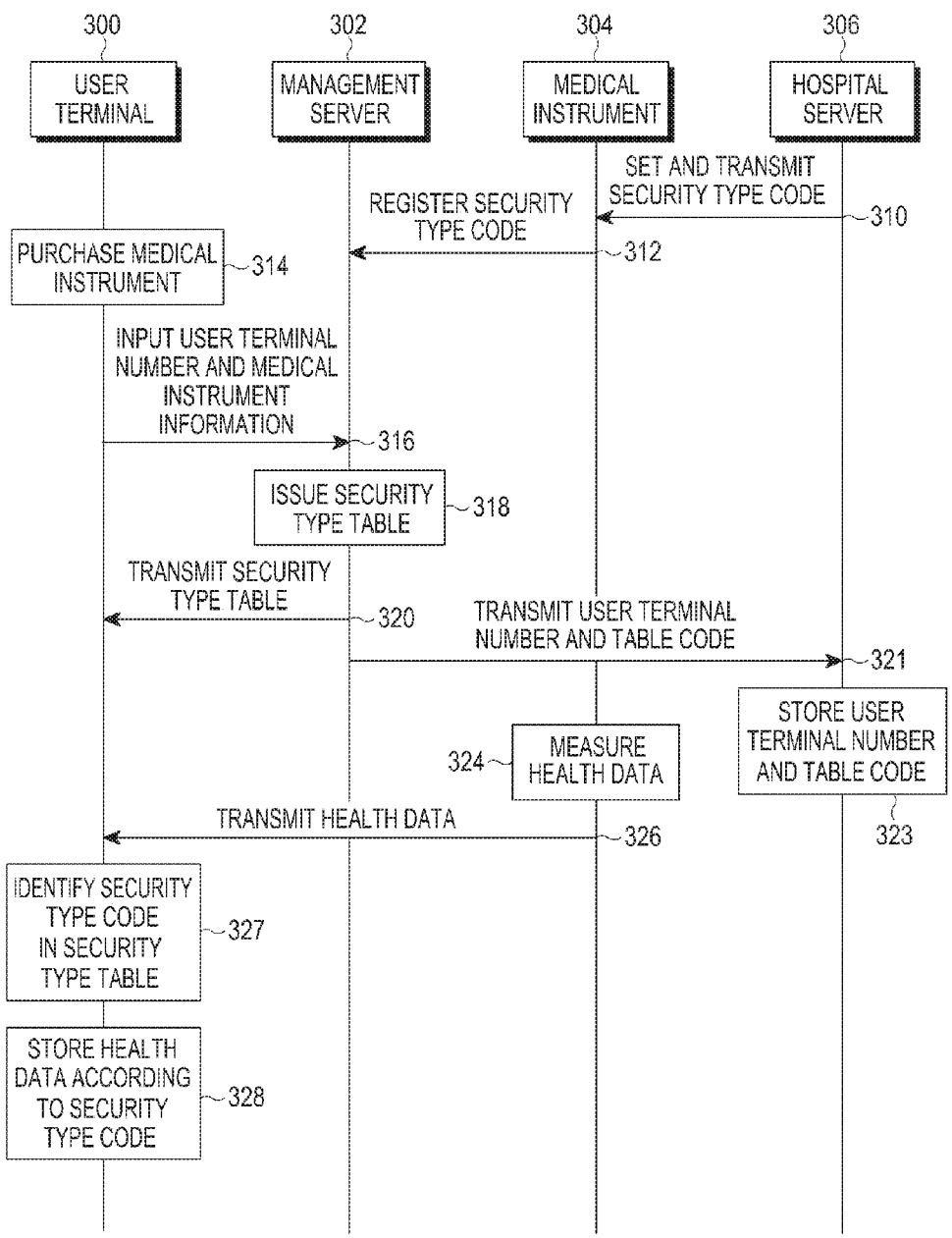
FIG. 3 is a signal flow diagram illustrating a procedure in which health data is stored and managed in a user terminal according to a first embodiment of the present disclosure.

FIG. 3 is a signal flow diagram illustrating a procedure in which health data is stored and managed in a user terminal according to a first embodiment of the present disclosure.

Referring to FIG. 3, the signal flow diagram includes a user terminal 300, a management server 302, a medical instrument 304, and a hospital server 306. In FIG. 3, a hospital server 306 sets a security type code of a medical instrument 304 interworked therewith, and transmits the security type code to the medical instrument 304 in operation 310. The medical instrument 304 registers the security type code in a management server 302 interworked therewith in operation 312.

Here, although the case in which the hospital server 306 sets the security type code of the medical instrument 304 is described as an example, the medical instrument 304 may directly set and transmit the security type code to the management server 302. Although not illustrated, the hospital server 306 may manage a Personal Health Record (PHR) server, and the PHR server may be located outside or inside the hospital server 306. Further, the PHR server may also set and transmit the security type code to the management server 302.

A user terminal 300, such as a smart phone, executes an application to purchase a medical instrument through a sensor shop in operation 314, and inputs a user terminal number and information of the purchased medical instrument to the management server 302 in operation 316. Here, the user terminal number corresponds to information for identifying the user terminal, and may be a phone number, a serial number, a preset user password, or the like.

Since the management server 302 recognizes in advance the security type code for the medical instrument 304 as described in operations 310 and 312, the management server 302 issues a security type table corresponding to medical instrument information at the same time when the medical instrument information is input in operation 318. The security type table is issued to be mapped onto the user terminal number, and since the security type table has been described with reference to FIGS. 1 and 2, a description of the security type table will be omitted. The security type table is issued to correspond to the medical instrument. When the medical instrument measures one health data, the security type table illustrated in FIG. 1 is issued, and when the medical instrument measures a plurality of health data, the security type table illustrated in FIG. 2 is issued.

The management server 302 transmits the security type table to the user terminal 300 in operation 320, and transmits the user terminal number received in operation 316 and the table code of the security type table to the hospital server 306 in operation 321. The hospital server 306 stores the user terminal number and the table code in operation 323.

Thereafter, when the medical instrument 304 measures health data in operation 324, the medical instrument 304 wiredly or wirelessly transmits the measured health data to the user terminal 300 (in operation 326, and in operation 327, the user terminal 300 determines a security type code denoting a security type of the health data measured through the medical instrument 304, in the security type table received in operation 320.

In operation 328, the user terminal 300 stores the received health data in a memory according to the security type code determined in operation 327. For example, when the security type code denoting the security type of the health data measured through the medical instrument 304 corresponds to '00', the user terminal 300 determines that the measured health data is general data which should be stored through an open mode, and stores the health data in a USIM chip which can be shared with anyone. On the other hand, when the security type code corresponds to '10', the user terminal 300 determines that the health data measured through the medical instrument 304 is security data which should be stored through a closed mode, and stores the health data in an EMID flash memory which can be shared with a specific group, such as a medical team.

As described above, when storing the health data measured through the medical instrument 304, the user terminal 300 stores the general data in the USIM chip and the security data in the EMID flash memory according to the security type code indicated in the security type table to basically prevent external access to the health data requiring security. Further, the security type table may be issued in the management server 302, and the security type code required for issuance of the security type table may be set through the medical instrument 304, the hospital server 306, or the PHR server.

Figure 4:
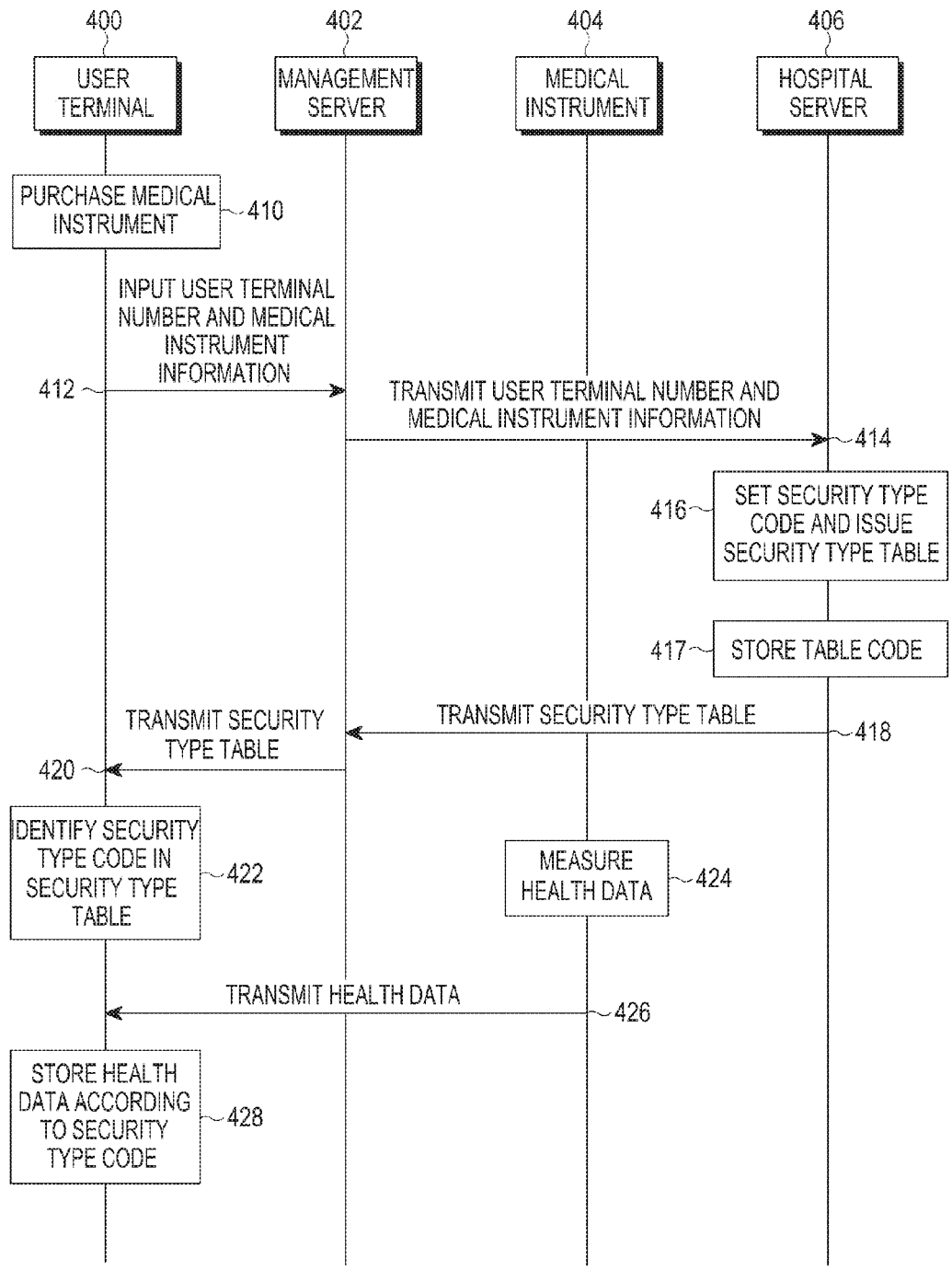
FIG. 4 is a signal flow diagram illustrating a procedure in which health data is stored and managed in a user terminal according to a second embodiment of the present disclosure.

FIG. 4 is a signal flow diagram illustrating a procedure in which health data is stored and managed in a user terminal according to a second embodiment of the present disclosure.

Referring to FIG. 4, the signal flow diagram includes a user terminal 400, a management server 402, a medical instrument 404, and a hospital server 406. In FIG. 4, a user terminal 400, such as a smart phone, executes an application to purchase a medical instrument 404 through a sensor shop in operation 410, and inputs a user terminal number and information of the purchased medical instrument to a management server 402 in operation 412. Here, the user terminal number corresponds to information for identifying the user terminal, and may be a phone number, a serial number, a preset user password, or the like.

Since the management server 402 does not recognize a security type code for the medical instrument 404, the management server 402 transmits the user terminal number and the medical instrument information to a hospital server 406 in order to acquire the security type code in operation

414. The hospital server 406 sets the security type code of the medical instrument 404 corresponding to the received medical instrument information, issues a security type table corresponding to the medical instrument 404 in operation 416, and stores a table code of the security type table in operation 417.

Since the security type table has been described with reference to FIGS. 1 and 2, a description of the security type table will be omitted. The security type table is issued to correspond to the medical instrument. When the medical instrument measures one health data, the security type table illustrated in FIG. 1 is issued, and when the medical instrument measures a plurality of health data, the security type table illustrated in FIG. 2 is issued. Further, although not illustrated, the hospital server 406 may manage a PHR server, and the PHR server may be located outside or inside the hospital server 406. Moreover, the PHR server may also set the security type code.

The hospital server 406 transmits the security type table to the management server 402 in operation 418, and the management server 402 transmits the received security type table to the user terminal 400 in operation 420. The user terminal 400 determines the security type code denoting the security type of the health data measured through the medical instrument 404, in the security type table in operation 422.

Thereafter, when the medical instrument 404 measures health data in operation 424, the medical instrument 404 wiredly or wirelessly transmits the measured health data to the user terminal 400 in operation 426, and the user terminal 400 stores the received health data in a memory according to the security type code determined in operation 428. For example, when the security type code denoting the security type of the health data measured through the medical instrument 404 corresponds to '00', the user terminal 400 determines that the measured health data is general data which should be stored through an open mode, and stores the health data in a USIM chip which can be shared with anyone. On the other hand, when the security type code corresponds to '10', the user terminal 400 determines that the health data measured through the medical instrument 404 is security data which should be stored through a closed mode, and stores the health data in an EMID flash memory which can be shared with a specific group, such as a medical team.

As described above, when storing the health data measured through the medical instrument 404, the user terminal 400 stores the general data in the USIM chip and the security data in the EMID flash memory according to the security type code indicated in the security type table to basically prevent external access to the health data requiring security. Further, the security type table may be issued in the management server 402, and the security type code required for issuance of the security type table may be set through the hospital server 406, or the PHR server.

The method in which the user terminal stores the corresponding health data in the EMID flash memory such that the health data can be shared with the specific group, such as a medical team, when the health data measured through the medical instrument corresponds to the security required data, has been described with reference to FIGS. 3 and 4. Hereinafter, a method in which the user terminal shares the health data stored in the EMID flash memory with the specific group, such as a medical team, for example, the hospital server, will be described with reference to FIG. 5.

Figure 5:
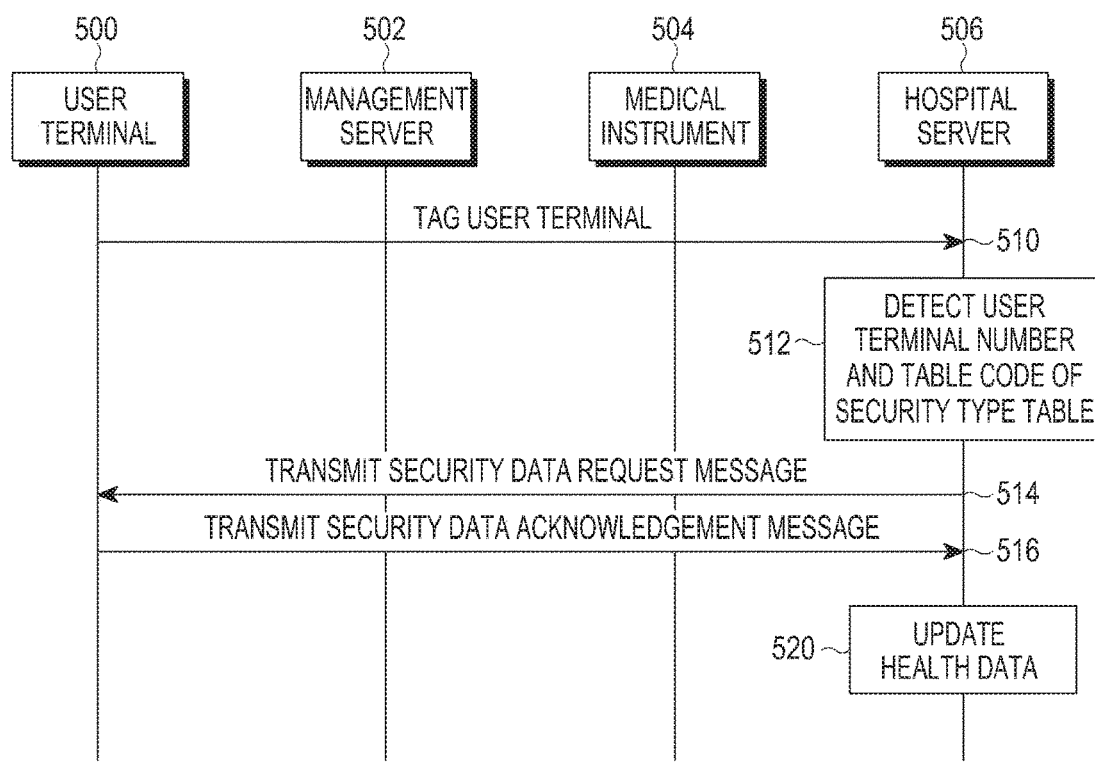
FIG. 5 is a signal flow diagram illustrating a procedure in which a user terminal and a hospital server share security required health data according to an embodiment of the present disclosure.

FIG. 5 is a signal flow diagram illustrating a procedure in which a user terminal and a hospital server share security required health data according to an embodiment of the present disclosure.

Referring to FIG. 5, the signal flow diagram includes a user terminal 500, a management server 502, a medical instrument 504, and a hospital server 506. In FIG. 5, a patient visits a hospital to tag the user terminal 500 at the hospital server 506 in operation 510, and the hospital server 506 detects a user terminal number and a table code of a security type table which the user terminal 500 manages in operation 512.

Although not illustrated, at this time, a hospital server 506 determines whether or not the determined table code coincides with a table code stored in advance, and when the determined table code coincides with the table code stored in advance, a security data stored in an EMID flash memory of the user terminal can be shared. The hospital server 506 has already recognized the table code of the security type table mapped onto the user terminal, and the table code stored in advance implies the table code of the security type table mapped onto the user terminal. Here, it is assumed that the detected table code coincides with the table code stored in advance.

In operation 514, the hospital server 506 transmits a security data request message for requesting sharing of the security data stored in the EMID flash memory of the user terminal 500 to the user terminal 500 when the table code detected in operation 512 coincides with the table code stored in advance. The user terminal 500 transmits the security data stored in the EMID flash memory to the hospital server 506 through a security data acknowledgement message for the security data request message in operation 516. For example, the user terminal 500 and the hospital server 506 share the security data stored in the EMID flash memory through operations 514 and 516. The hospital server 506 updates the health data of the user terminal 500 according to the shared health data in operation 520.

However, when the table code detected in operation 512 does not coincide with the table code stored in advance, the hospital server 506 cannot share the security data stored in the EMID flash memory of the user terminal 500.

Figure 6:
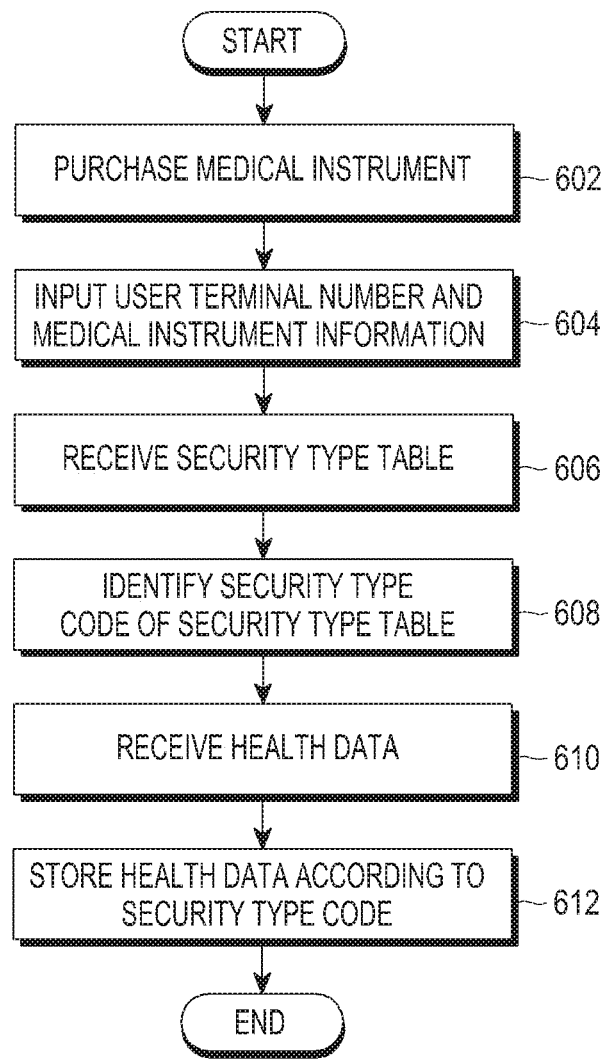
FIG. 6 is a flowchart illustrating an operation of a user terminal for storing and managing health data according to an embodiment of the present disclosure.

FIG. 6 is a flowchart illustrating an operation of a user terminal for storing and managing health data according to an embodiment of the present disclosure.

Referring to FIG. 6, a user terminal, for example, a smart phone executes an application to purchase a medical instrument through a sensor shop in operation 602, and proceeds to operation 604 to input a user terminal number and medical instrument information to a management server. Here, the user terminal number corresponds to information for identifying the user terminal, and may be a phone number, a serial number, a preset user password, or the like.

The user terminal receives a security type table from the management server in operation 606, and proceeds to operation 608 to determine a security type code of the security type table. The security type code is a code denoting that data measured through the medical instrument purchased in operation 602 is general data which should be stored through an open mode, or security data which should be stored through a closed mode.

In operation 610, the user terminal receives health data measured through the medical instrument purchased in operation 602. In operation 612, the user terminal stores the received health data according to security type code determined in operation 608. For example, when the security type code determined in operation 608 corresponds to '00', the user terminal stores the measured health data in a USIM chip which can be shared with anyone, and when the security type code corresponds to '10', the user terminal stores the measured health data in an EMID flash memory which can be shared with a specific group, such as a medical team.

Figure 7:
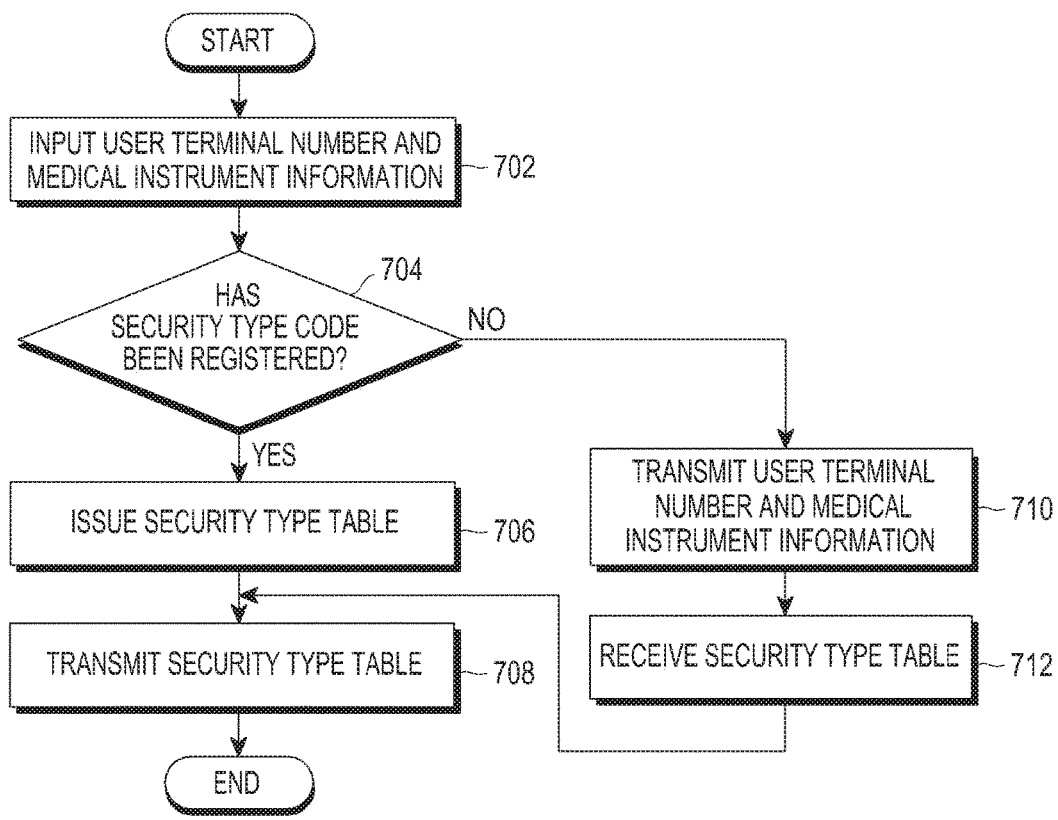
FIG. 7 is a flowchart illustrating an operation of a management server for storing and managing health data according to an embodiment of the present disclosure.

FIG. 7 is a flowchart illustrating an operation of a management server for storing and managing health data according to an embodiment of the present disclosure.

Referring to FIG. 7, a management server receives a user terminal number and information of a medical instrument purchased through a user terminal, from the user terminal in operation 702. The management server determines whether or not a security type code for health data measured through the medical instrument has been registered in operation 704, and when the security type code has been registered, proceeds to operation 706 to issue a security type table, mapped onto the user terminal number, based on the registered security type code. Thereafter, the management server transmits the security type table to the user terminal in operation 708. In the determined result of operation 704, the case in which the security type code has been registered corresponds to a case in which the management server has recognized in advance the security type code for the medical instrument as described with reference to FIG. 3.

Meanwhile, when it is determined in operation 704 that the security type code has not been registered, the management server proceeds to operation 710 to transmit the user terminal number and the medical instrument information to a hospital server. The management server receives a security type table issued and transmitted from the hospital server in operation 712. In the determined result of operation 704, the case in which the security type code has not been registered corresponds to a case in which the management server has not recognized the security type code for the medical instrument as described with reference to FIG. 4.

Figure 8:
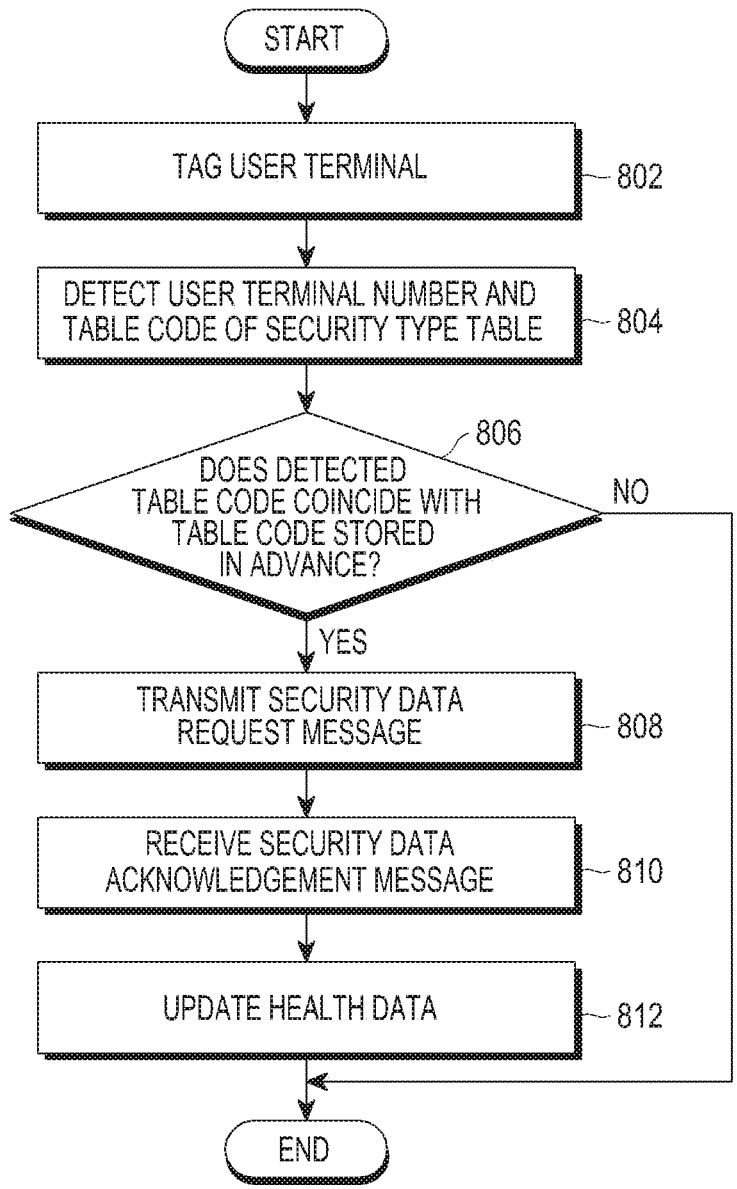
FIG. 8 is a flowchart illustrating an operation through which a hospital server shares security required health data with a user terminal according to an embodiment of the present disclosure.

FIG. 8 is a flowchart illustrating an operation through which a hospital server shares security required health data with a user terminal according to an embodiment of the present disclosure.

Referring to FIG. 8, a hospital server tags a user terminal in operation 802, and proceeds to operation 804 to detect a user terminal number of the user terminal, and a table code of a security type table managed through the user terminal. The hospital server determines whether or not the detected table code coincides with a table code stored in advance, in operation 806. Here, the table code stored in advance implies a table code of the security type table mapped onto the user terminal.

When it is determined in operation 806 that the table code detected in operation 804 coincides with the table code stored in advance, the hospital server proceeds to operation 808 to transmit a security data request message for requesting sharing of a security data stored in an EMID flash memory of the user terminal. The hospital server receives the security data stored in the EMID flash memory through a security data acknowledgement message in operation 810, and proceeds to operation 812 to update the health data of the user terminal.

However, when it is determined in operation 806 that the table code detected in operation 804 does not coincide with the table code stored in advance, the hospital server cannot share the security data stored in the EMID flash memory with the user terminal.

Figure 9:
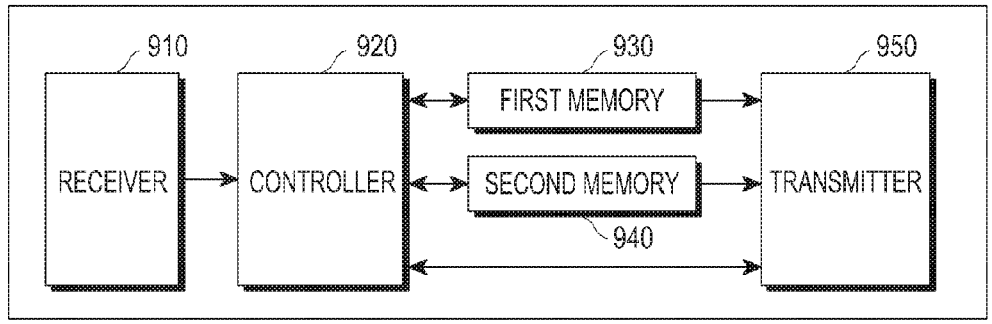
FIG. 9 is a block diagram illustrating a configuration of a user terminal for storing and managing health data according to an embodiment of the present disclosure.

FIG. 9 is a block diagram illustrating a configuration of a user terminal for storing and managing health data according to an embodiment of the present disclosure.

Referring to FIG. 9, a user terminal 900 includes a receiver 910, a controller 920, a first memory 930, a second memory 940, and a transmitter 950.

When purchasing a medical instrument, the user terminal 900 transmits and inputs a user terminal number and medical instrument information to a management server through the transmitter 950, and receives a security type table from the management server through the receiver 910. Here, the user terminal number corresponds to information for identifying the user terminal, and may be a phone number, a serial number, a preset user password, or the like.

The controller 920 identifies a security type code of a security type table when the security type table is transferred from the receiver 910. Thereafter, the controller 920 controls the first and the second memories 930 and 940, respectively, according to the previously determined security type code when health data is transferred from the receiver 910. For example, when the health data is transferred from the receiver 910, the controller 920 controls such that the health data is stored in a USIM chip which can be shared with anyone, when the previously determined security type code corresponds to '00', and the health data is stored in an EMID flash memory which can be shared with a specific group, such as a medical team, when the security type code corresponds to '10'.

Figure 10:
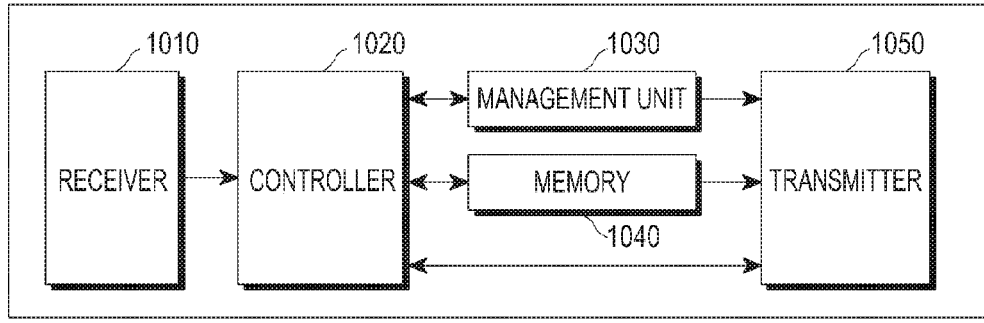
FIG. 10 is a block diagram illustrating a configuration of a management server for storing and managing health data according to an embodiment of the present disclosure.

FIG. 10 is a block diagram illustrating a configuration of a management server for storing and managing health data according to an embodiment of the present disclosure.

Referring to FIG. 10, a management server 1000 includes a receiver 1010, a controller 1020, a management unit 1030, a memory 1040, and a transmitter 1050.

The receiver 1010 of the management server 1000 determines through the controller 1020 whether or not a security type code of a security type table mapped onto a user terminal has been registered in the memory 1040, when a user terminal number and information of a medical instrument purchased through the user terminal are input from the user terminal. At this time, when it is determined that the security type code has been registered in the memory 1040, the security type table is issued through the management unit 1030 to be transmitted to the user terminal through the transmitter 1050. Further, the user terminal number and the table code of the security type table are transmitted to a hospital server through the transmitter 1050.

Meanwhile, when it is determined that the security type code has not been registered in the memory 1040, the user terminal number and the medical instrument information are transmitted to the hospital server through the transmitter 1050. Thereafter, a security type table transmitted from the hospital server is received through the receiver 1010, and the received security type table is transmitted to the user terminal through the transmitter 1050.

Figure 11:
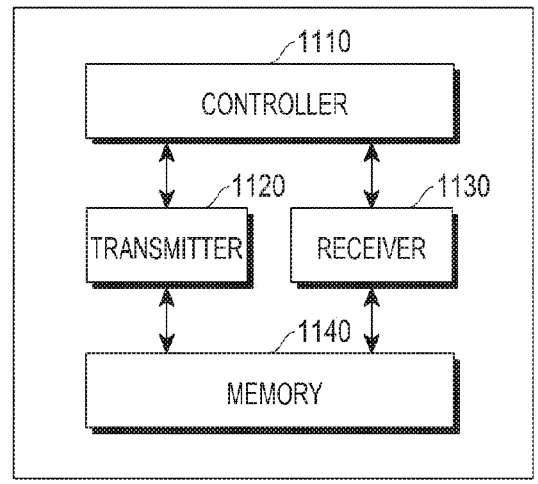
FIG. 11 is a block diagram illustrating a configuration of a hospital server for sharing security required health data with a user terminal according to an embodiment of the present disclosure.

FIG. 11 is a block diagram illustrating a configuration of a hospital server for sharing security required health data with a user terminal according to an embodiment of the present disclosure.

Referring to FIG. 11, a hospital server 1100 includes a controller 1110, a transmitter 1120, a receiver 1130, and a memory 1140.

The receiver 1130 of the hospital server 1100 determines a user terminal number and a table code through the controller 1110 when the user terminal number and the table code of a security type table which a user terminal manages are input through tagging of the user terminal.

Moreover, the controller 1110 determines whether or not the determined table code coincides with a table code stored in advance, that is, a table code of a security type table mapped onto the user terminal, and when the determined table code coincides with the table code stored in advance, transmits a security data request message for requesting sharing of a security data stored in an EMID flash memory of the user terminal through the transmitter 1120.

Thereafter, a security data acknowledgement message is received in reply to the security data request message through the receiver 1130, and the security data stored in the EMID flash memory of the user terminal is received together with the security data acknowledgement message. The received security data is transferred to the memory 1140, and the hospital server 1100 updates health data of the user terminal which is stored in the memory 1140.

The foregoing method for processing a user-customized page of the present disclosure may be implemented in an executable program command form by various computer means and be recorded in a non-transitory computer readable recording medium. In this case, the non-transitory computer readable recording medium may include a program command, a data file, and a data structure individually or a combination thereof. In the meantime, the program command recorded in a recording medium may be specially designed or configured for the present disclosure or be known to a person having ordinary skill in a computer software field to be used. The non-transitory computer readable recording medium includes Magnetic Media, such as a hard disk, a floppy disk, or a magnetic tape, an Optical Media, such as a Compact Disc Read Only Memory (CD-ROM) or a Digital Versatile Disc (DVD), a Magneto-Optical Media, such as a floptical disk, and a hardware device, such as a ROM, a Random Access Memory (RAM), a flash memory for storing and executing program commands. The non-transitory computer readable recording medium can also be distributed over network coupled computer systems so that the computer readable code is stored and executed in a distributed fashion. Further, the program command includes a machine language code created by a complier and a high-level language code executable by a computer using an interpreter. The foregoing hardware device may be configured to be operated as at least one software module to perform an operation of the present disclosure.

Further, it may be appreciated that an apparatus and a method for managing health data according to embodiments of the present disclosure can be implemented in software, hardware, or a combination thereof. For example, specific electronic components may be employed in a mobile device or similar or related circuitry for implementing the functions associated with the various embodiments of the present disclosure as described above. Alternatively, one or more processors operating in accordance with stored instructions may implement the functions associated with the various embodiments of the present disclosure as described above. If such is the case, it is within the scope of the present disclosure that such instructions may be stored on one or more non-transitory processor readable mediums. Examples of the processor readable mediums include a volatile or a non-volatile storage device, such as a ROM, a memory such as a RAM, a memory chip, a memory device, or a memory Integrated Circuit (IC), or a recordable optical or magnetic medium, such as a CD, a DVD, a magnetic disk, or a magnetic tape, regardless of its ability to be erased or its ability to be re-recorded. The processor readable mediums can also be distributed over network coupled computer systems so that the instructions are stored and executed in a distributed fashion. In addition, functional computer programs, instructions, and instruction segments for accomplishing the present disclosure can be easily construed by programmers skilled in the art to which the present disclosure pertains.

Accordingly, the present disclosure includes a program for a code implementing the apparatus and method described in the appended claims of the specification and a machine (i.e., a computer or the like)-readable storage medium for storing the program. Moreover, such a program as described above can be electronically transferred through an arbitrary medium, such as a communication signal transferred through a cable or a wireless connection, and the present disclosure properly includes their equivalents.

Moreover, an apparatus for health data management may receive the program from a program providing apparatus connected in a wired or wireless method, and store the program. The program providing apparatus may include a program including instructions allowing a graphic processing apparatus to perform a preset content protecting method, a memory for storing information used for the content protecting method, a communication unit for performing a wired or a wireless communication with the graphic processing apparatus, and a controller for transmitting a corresponding program to a transmitter/receiver in response to a request of the graphic processing apparatus or automatically.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A method for managing health data by a user terminal, the method comprising:
   transmitting information of the user terminal for identifying the user terminal, and information of a medical instrument for measuring the health data to a management server interworked with the user terminal;
   receiving information comprising a security type for instructing the health data measured by the medical instrument to be stored in a first memory or a second memory, the second memory being accessible by at least one designated user, from the management server; and
   storing the health data in the first memory or the second memory based on the security type.

2. The method of claim 1,
   wherein the security type is included in a security type table, and
   wherein the security type table comprises at least one of a table code for identification of the security type table, slot numbers of slots constituting the first and the second memories, identifiers for identifying vendors of the first and the second memories, or usage codes of the slots.

3. The method of claim 1,
   wherein the security type is set based on medical instruments if the medical instrument measures one health data, and
   wherein the security type is set based on health data, which the medical instrument measures, if the medical instrument measures two or more health data.

4. The method of claim 1,
   wherein the security type table is received from the management server or a hospital server interworked with the management server,
   wherein the security type is set in the medical instrument or the hospital server to be registered in the management server, if the security type table is received from the management server, and wherein the security type is set in the hospital server, if the security type table is received from the hospital server.

5. The method of claim 1, further comprising:
receiving a request for sharing of the health data stored in the second memory, from a hospital server interworked with the management server, if a table code of the security type table coincides with a table code of a security type table mapped onto the information of the user terminal; and
transmitting the health data stored in the second memory to the hospital server.

6. The method of claim 1, wherein the information of the user terminal comprises at least one of a phone number, a serial number, or a preset password of the user terminal.

7. A method for managing health data by a management server interworked with a user terminal, the method comprising:
receiving information of the user terminal for identifying the user terminal and information of a medical instrument for measuring the health data, from the user terminal;
determining whether or not a security type for instructing the health data measured by the medical instrument to be stored in a first memory or a second memory is registered in the management server, the second memory being accessible by at least one designated user;
generating information comprising the security type, if the security type is registered in the management server; and
transmitting the information to the user terminal.

8. The method of claim 7, further comprising:
transmitting the information of the user terminal and the information of the medical instrument to a hospital server in which the security type is stored, if the security type is not registered in the management server; and
receiving a security type table from the hospital server, and transmitting the received security type table to the user terminal.

9. The method of claim 7,
wherein the security type is included in a security type table, and
wherein the security type table comprises at least one of a table code for identification of the security type table, slot numbers of slots constituting the first and the second memories, identifiers for identifying vendors of the first and the second memories, or usage codes of the slots.

10. The method of claim 7,
wherein the security type is set based on medical instruments if the medical instrument measures one health data, and
wherein the security type is set based on health data which the medical instrument measures, if the medical instrument measures two or more health data.

11. The method of claim 7, wherein the security type is set in the medical instrument or a hospital server to be registered in the management server.

12. The method of claim 7, wherein the information of the user terminal comprises at least one of a phone number, a serial number, or a preset password of the user terminal.

13. A user terminal for managing health data, the user terminal comprising:
a first memory;
a second memory being accessible by at least one designated user;
a transmitter configured to transmit information of the user terminal for identifying the user terminal and information of a medical instrument for measuring the health data to a management server interworked with the user terminal;
a receiver configured to:
receive information comprising a security type for instructing the health data measured by the medical instrument to be stored in the first memory or the second memory, from the management server, and
receive the health data from the medical instrument; and
at least one processor configured to instruct the health data to be stored in the first memory or the second memory based on the security type.

14. The user terminal of claim 13,
wherein the security type is included in a security type table, and
wherein the security type table comprises at least one of a table code for identification of the security type table, slot numbers of slots constituting the first and the second memories, identifiers for identifying vendors of the first and the second memories, or usage codes denoting usage of the slots.

15. The user terminal of claim 14,
wherein the security type table is received from the management server or a hospital server interworked with the management server,
wherein the security type is set in the medical instrument or the hospital server to be registered in the management server, if the security type table is received from the management server, and
wherein the security type is set in the hospital server, if the security type table is received from the hospital server.

16. The user terminal of claim 14,
wherein the receiver receives a request for sharing of the health data stored in the second memory, from a hospital server interworked with the management server, if a table code of the security type table coincides with a table code of a security type table mapped onto the information of the user terminal, and
wherein the transmitter transmits the health data stored in the second memory to the hospital server.

17. The user terminal of claim 13,
wherein the security type is set based on medical instruments if the medical instrument measures one health data, and
wherein the security type is set based on health data, which the medical instrument measures, if the medical instrument measures two or more health data.

18. The user terminal of claim 13, wherein the information of the user terminal comprises at least one of a phone number, a serial number, or a preset password of the user terminal.

19. A management server for managing health data, the management server comprising:
a receiver configured to receive information of the a user terminal for identifying a user terminal and information of a medical instrument for measuring the health data, from the user terminal;
at least one processor configured to:
determine whether or not a security type for instructing the health data measured by the medical instrument to be stored in a first memory or a second memory is registered in the management server, the second memory being accessible by at least one designated user, and generate information comprising the security type, if the security type is registered in the management server; and a transmitter configured to transmit the information to the user terminal.

20. The management server of claim 19, wherein the transmitter is further configured to:

transmit the information of the user terminal and the information of the medical instrument to a hospital server in which the security type is stored, if the security type is not registered in the management server, and transmit a security type table to the user terminal if the receiver receives the security type table from the hospital server.

21. The management server of claim 19, wherein the security type is included in a security type table, and wherein the security type table comprises at least one of a table code for identification of the security type table, slot numbers of slots constituting the first and the second memories, identifiers for identifying vendors of the first and the second memories, or usage codes of the slots.

22. The management server of claim 19, wherein the security type is set based on medical instruments if the medical instrument measures one health data, and wherein the security type is set based on health data which the medical instrument measures if the medical instrument measures two or more health data.

23. The management server of claim 19, wherein the security type is set in the medical instrument or a hospital server to be registered in the management server.

24. The management server of claim 19, wherein the information of the user terminal comprises at least one of a phone number, a serial number, or a preset password of the user terminal.

25. A non-transitory processor readable medium for storing a computer program of instructions configured to be readable by at least one processor for instructing the at least one processor to execute a computer process for performing a method for managing health data in a user terminal, the method comprising:

transmitting information of the user terminal for identifying the user terminal, and information of a medical instrument for measuring the health data to a management server interworked with the user terminal;

receiving information comprising a security type for instructing the health data measured by the medical instrument to be stored in a first memory or a second memory, from the management server, the second memory being accessible by at least one designated user; and storing the health data in the first memory or the second memory based on the security type.

* * * * *